United States Patent [19]
Fulmer et al.

[11] Patent Number: 5,709,742
[45] Date of Patent: *Jan. 20, 1998

[54] REACTIVE TRICALCIUM PHOSPHATE COMPOSITIONS

[75] Inventors: Mark Fulmer, San Jose; Brent R. Constantz, Los Gatos; Ira C. Ison, Campbell; Bryan M. Barr, San Jose, all of Calif.

[73] Assignee: Norian Corporation, Cupertino, Calif.

[*] Notice: The term of this patent shall not extend beyond the expiration date of Pat. No. 5,571,493.

[21] Appl. No.: 648,318

[22] Filed: May 15, 1996

Related U.S. Application Data

[63] Continuation of Ser. No. 334,519, Nov. 4, 1994, Pat. No. 5,569,442.

[51] Int. Cl.$^6$ .................................. C04B 12/02
[52] U.S. Cl. .................................. 106/690
[58] Field of Search .................. 423/309, 308, 423/311; 106/35, 690

[56] References Cited

U.S. PATENT DOCUMENTS

| | | |
|---|---|---|
| 2,095,994 | 10/1937 | MacIntire . |
| 4,612,986 | 9/1986 | Brown et al. . |
| 4,693,986 | 9/1987 | Vit et al. . |
| 5,053,212 | 10/1991 | Constantz et al. . |
| 5,152,836 | 10/1992 | Hirano et al. . |
| 5,178,845 | 1/1993 | Constantz et al. ............ 423/309 |
| 5,322,675 | 6/1994 | Hakamatsuka et al. . |
| 5,338,356 | 8/1994 | Hirano et al. ............ 106/690 |
| 5,525,148 | 6/1996 | Chow et al. ............ 423/311 |
| 5,571,493 | 11/1996 | Fulmer et al. ............ 423/308 |
| 5,580,623 | 12/1996 | Fulmer et al. ............ 106/35 |

FOREIGN PATENT DOCUMENTS

| | | |
|---|---|---|
| 2143733 | 9/1995 | Canada . |
| 0 639 366 A1 | 2/1995 | European Pat. Off. . |
| 2 195 586 | 8/1973 | France . |
| 2 537 558 | 10/1983 | France . |
| 2 693 716 | 7/1992 | France . |
| 59 088 351 | 5/1984 | Japan . |
| 36404 | 2/1985 | Japan . |
| 2-75006 | 11/1987 | Japan . |
| 1-00005 | 5/1988 | Japan . |
| 1-250864 | 5/1991 | Japan . |
| 3 112 838 | 5/1991 | Japan . |
| 3-174349 | 7/1991 | Japan . |
| 92-12044 | 1/1992 | Japan . |
| 4-348754 | 12/1992 | Japan . |
| 4-348755 | 12/1992 | Japan . |
| 5-23386 | 2/1993 | Japan . |
| 5-9383 | 2/1993 | Japan . |
| 5-319891 | 12/1993 | Japan . |
| 6-45494 | 6/1994 | Japan . |
| 1 388 236 | 3/1975 | United Kingdom . |
| 2 132 991 | 7/1984 | United Kingdom . |
| WO 95/08304 | 3/1995 | WIPO . |
| WO 95/08319 | 3/1995 | WIPO . |

OTHER PUBLICATIONS

Mirtchi et al., Biomaterial (1991) 12:505.
Mirtchi et la. Biomaterials (1989) 10: 475.
Mirtchi et al. Biomaterials (1990) 11:84.

(List continued on next page.)

*Primary Examiner*—Wayne Langel
*Attorney, Agent, or Firm*—Townsend and Townsend and Crew LLP; Bret E. Field

[57] ABSTRACT

Methods for producing a room temperature stable, phase pure $\alpha$-$C_3P$ product, and compositions derived therefrom, are provided. In the subject method, a tricalcium phosphate source is heated to a temperature sufficient to convert substantially all of said tricalcium phosphate source to a substantially phase pure $\alpha$-$C_3P$ product. The temperature of the resultant product is rapidly cooled to a temperature below about 700° C., resulting in a room temperature stable, reactive $\alpha$-$C_3P$ product. The resultant $\alpha$-$C_3P$ product may be milled to provide an $\alpha$-$C_3P$ composition which may find use in the preparation of calcium phosphate cements.

13 Claims, 4 Drawing Sheets

OTHER PUBLICATIONS

Wang, "Treatise on Materials Science and Technology", *Academic Press* (1976), 9:iii–33.

Bhavnagary et al., "Preparation of Tri–calcium Phosphate by Hydrolysis of Diacalcium Phosphate with Calcium Hydroxide," *J. Appl. Chem. Biotechnol.* (1977), 27:393–398.

Monma, et al., "Properties of Hydroxyapatite Prepared by the Hydrolysis of Tricalcium Phosphate", *J. Chem. Tech. Biotechnol.* (1981), 31:15–24.

Richerson, "Modern Ceramic Engineering, Properties, Processing, and Use in Design", *Marcel Dekker, Inc.* (1982), 147–177.

Lemaitre, et al., "Calcium Phosphate Cements for Medical Use: State of the Art and Perspectives of Development", *Silicates Industriales* (1987), 141–146.

Monma, "On Hydraulic Calcium Phosphates", *MRS Int'l. Mtg. on Adv. Mats., Materials Research Society* (1989), 13:15–25.

Iijima, et al., "Properties of Apatite Cement Composed of α–Tricalcium Phosphate and Tetracalcium Phosphate", *Gysum & Lime* (1992), 238:159.

REACTIVE TRICALCIUM PHOSPHATE COMPOSITIONS

This is a continuation of application Ser. No. 08/334,519 filed 4 Nov. 1994, U.S. Pat. No. 5,569,442.

INTRODUCTION

1. Technical Field

The field of this invention is calcium phosphate cements.

2. Background

Calcium phosphate minerals are primary inorganic components of naturally occurring bone. Much of the calcium phosphate in bone is present as hydroxyapatite or modified forms thereof such as dahllite (a carbonate substituted form of hydroxyapatite). When naturally occurring bone becomes deteriorated or broken, it is often desirable to replace the defective bone with a bone substitute material. Because hydroxyapatite and substituted forms thereof closely resemble calcium phosphate mineral found in naturally occurring bone, both chemically and structurally, synthetic hydroxyapatites are attractive materials for use in bone repair and replacement.

Synthetic hydroxyapatites may be fabricated from calcium phosphate mineral cements which comprise dry and wet components, where the components are mixed to form a kneadable product which then sets into a solid mass. The dry ingredients found in such cements may comprise a phosphoric acid source and a calcium source. U.S. Patents which describe various cements suitable for use in preparing calcium phosphate minerals include U.S. Pat. Nos. 4,880,610; 5,047,031; 5,129,905; 5,053,212; and 5,178,845, the disclosures of which are herein incorporated by reference.

The setting times and compressive strengths of calcium phosphate cements can be affected by the various calcium sources with which they are prepared. For example, when tricalcium phosphate is included as a calcium source in the cement precursor, cements with high compressive strengths are obtained. In addition, using tricalcium phosphates in cement preparation provides cements with more consistently reproducible characteristics. It has also been observed that cements prepared from tricalcium phosphate are more physiologically compatible in terms of pH.

Despite the advantages of using tricalcium phosphate as a calcium source in the preparation of calcium phosphate mineral cements, there are problems associated with using currently available sources of tricalcium phosphate. For example, cements prepared using tricalcium phosphates, which consist primarily of beta tricalcium phosphate, typically require long setting times which makes them impractical for use in many applications, including applications where the cement is intended to set in situ. Furthermore, many currently available sources of tricalcium phosphate are not phase pure, e.g. they also comprise sintered hydroxyapatite, which may result in a cement with poor strength and setting characteristics.

Thus, there is interest in the development of new tricalcium phosphate sources which are stable at room temperatures and, when used as a calcium source in the preparation of calcium phosphate cements, provide cements which set relatively quickly into calcium phosphate minerals with high compressive strength.

RELEVANT LITERATURE

Patents of interest include U.S. Patent Nos. 3,787,900; 3,913,229; 3,679,360; 4,097,935; 4,481,175; 4,503,157; 4,612,053; 4,659,617; and 4,693,986. See also U.K. Pat. App. GB 2,248,232-A, which describes a hydraulic calcium phosphate composition comprising alpha and beta tricalcium phosphates and Japanese Pat. No. 3-112838. See Gregory et al., *J. Res. N.B.S.* (1974) 74: 667–674. Chow, *Cer. Soc. of Jap.* (1991) 99: 954–964. See also, Arends and Jongebloed, *Rec. Trav. Chim. Pays-Bas* (1981) 100:3–9. Use of calcium phosphate as a sealer-filler material is described in Chohayeb et al., *J. Endodontics* (1987) 13:384–387. See also, Ohwaki et al., *13th Ann. Mtg. of the Soc. for Biomaterials*, Jun. 2–6, 1987, New York, N.Y., p209.

SUMMARY OF THE INVENTION

Methods are provided for the production of a room temperature stable, substantially phase pure alpha tricalcium phosphate ($\alpha$-$C_3P$). In the subject method, a tricalcium phosphate source is heated to a temperature sufficient to convert the tricalcium phosphate to substantially phase pure $\alpha$-$C_3P$. The resultant phase pure $\alpha$-$C_3P$ is quenched, resulting in a room temperature stable, phase pure or $\alpha$-$C_3P$ product. The resultant $\alpha$-$C_3P$ product may be milled to provide a reactive or $\alpha$-$C_3P$ composition which is suitable for use as a calcium source in the preparation of calcium phosphate mineral cements.

DESCRIPTION OF THE SPECIFIC EMBODIMENTS

Figure 1:
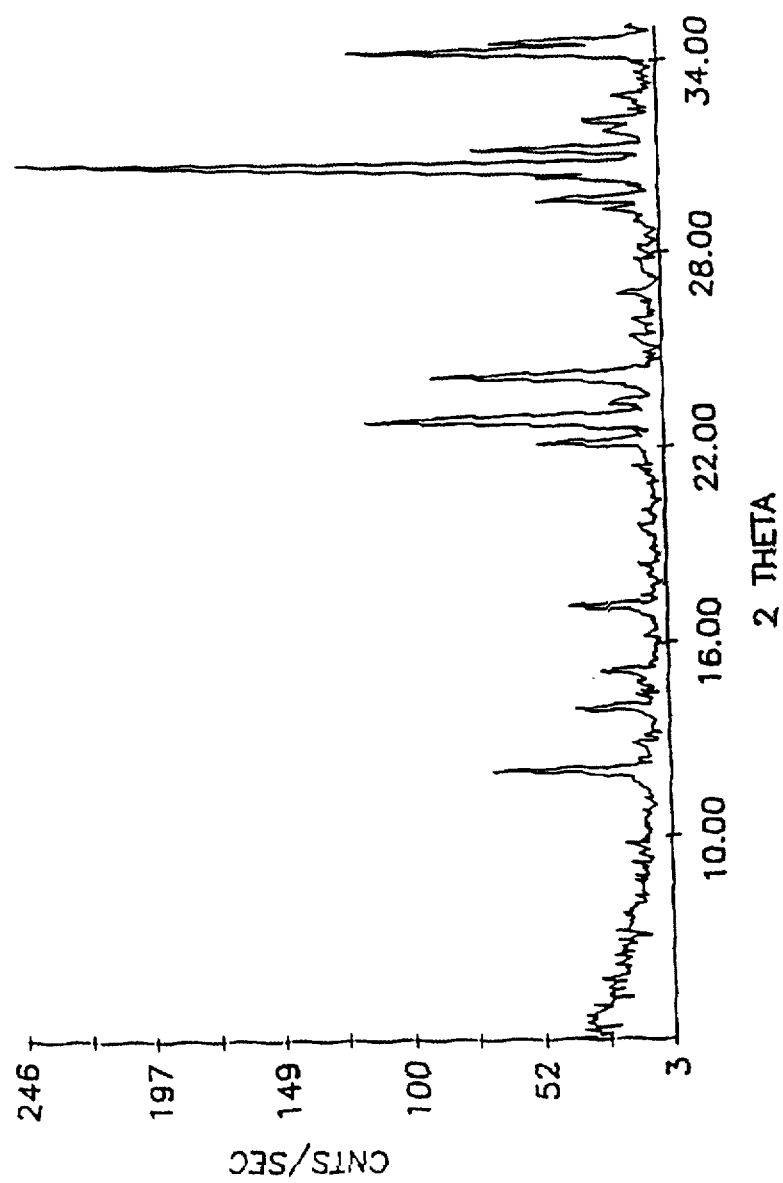
FIG. 1 is an X-ray diffraction pattern for room temperature stable, phase pure $\alpha$-$C_3P$ product prepared in accordance with the subject invention.

Methods are provided for producing substantially phase pure, reactive $\alpha$-$C_3P$ products. In the subject method, a tricalcium phosphate source is heated to a temperature sufficient to convert at least substantially all of the tricalcium phosphate source to a substantially phase pure $\alpha$-$C_3P$ product. The substantially phase pure $\alpha$-$C_3P$ product is then quenched, resulting in a room temperature stable, substantially phase pure $\alpha$-$C_3P$ product. The quenched $\alpha$-$C_3P$ product may then be milled to obtain an $\alpha$-$C_3P$ composition which finds use in the preparation of calcium phosphate mineral cements.

The first step of the subject method is to heat a source of tricalcium phosphate to convert at least substantially all of the tricalcium phosphate to $\alpha$-$C_3P$. The tricalcium phosphate source will typically be $\beta$-$C_3P$. $\beta$-$C_3P$ is available from a variety of commercial sources, but may also be prepared from readily available reactants. For example, $\beta$-$C_3P$ may be prepared by first combining stoichiometric amounts of $CaHPO_4$ and $CaCO_3$ to get a resultant product which has a calcium to phosphate ratio of 1.5:1. The stoichiometric amounts of $CaHPO_4$ and $CaCO_3$ are added to an aqueous reaction volume. The solids in the resultant slurry are then separated from the liquids under pressure, where the pressure may range from about 5–30 psi, more usually from about 5 to 25 psi and typically from about 8 to 15 psi.

In converting at least substantially all of the tricalcium phosphate source to phase pure α-C₃P, the tricalcium phosphate is directly heated to a temperature sufficient to convert substantially all of the tricalcium phosphate source to α-C₃P. Typically, the temperature will range from between about 1200° C. to 1700° C., more usually in the range of about 1250° C. to 1500° C., and will preferably be at about 1400° C. The elevated temperature is maintained at a relatively constant value in the indicated range to permit the crystal lattice phase to undergo a substantially uniform, polymorphic transition to the α-C₃P phase. A substantially uniform transition to the α-C₃P phase may be defined as the point at which at least about 80 percent, generally at least about 90 percent, and preferably at least about 95 percent, more preferably at least 99 percent of the initial tricalcium phosphate source has been converted to α-C₃P as measured by X-ray diffraction (XRD) analysis.

Heating of the tricalcium phosphate source can be achieved with furnaces such as cupola furnaces, crucible furnaces, open-hearth furnaces, induction furnaces, electric-arc furnaces, or the like. Once the desired temperature range is reached, thermodynamic crystal transition to the desired α-C₃P will usually occur in about 1 to 8 hours, more usually in about 2 to 6 hours, and typically in about 4 hours. The resulting α-C₃P product is usually in the form of a solid mass.

After substantially all of the tricalcium phosphate source has been converted to α-C₃P, the α-C₃P is cooled (quenched) by rapidly lowering the temperature of the heated α-C₃P by an amount of at least about 300° C., and usually by an amount of at least about 600° C., and more usually by an amount of at least about 700 ° C. The temperature of the solid α-C₃P will be quenched to a temperature between about −80° C. to about 900° C., usually to a temperature between about 0° C. to about 700° C., more usually to a temperature between about 0° C. and about 200° C., particularly to a temperature between about 0° C. and about 60° C., and typically room temperature. Temperature quenching results in an α-C₃P product that remains stable at room temperatures.

Any convenient means for quenching the heated, phase pure α-C₃P may be employed. Quenching means which find use include placing the heated α-C₃P product in a forced flow of cool gas or liquid, placing the heated α-C₃P product on a heat sink with high heat conductivity and thermal mass (a cold metal plate), and the like. Rapid cooling may also be facilitated by mechanically breaking-up the heated α-C₃P product to provide a greater surface area, and therefore an enhanced cooling profile. The material may also be splat quenched between two cold plates of high thermal conductivity and mass in order to more immediately draw the heat from the α-C₃P. Generally, rapidly cooling or temperature quenching the α-C₃P product to the desired temperature range will take less then about 2 hours, usually less then about 45 minutes, and more usually less then about 10 minutes.

Producing phase pure α-C₃P may be facilitated by the stabilization of the high temperature phase through the introduction of ionic (either anionic or cationic) additives into the tricalcium phosphate source. These additives may include alkali or alkaline earth metal salts, particularly with anions such as phosphates and sulphates, or other ions that may further enhance the stability of α-C₃P during the temperature quenching step. When these stabilization agents are incorporated in the tricalcium phosphate source, the ratio of agent to tricalcium phosphate will usually range from 0.001 to 5%, and preferably from 0.01 to 1%.

The resultant substantially phase pure α-C₃P is room temperature stable. By substantially phase pure is meant that the product will be at least about 80 percent, generally at least about 90 percent, and preferably at least about 95 percent, more preferably at least 99 percent α-C₃P. Purity of the resultant α-C₃P may be confirmed by XRD analysis, where a phase pure α-C₃P product will have an XRD pattern similar to the one shown in FIG. 1.

The resultant room temperature stable, substantially phase pure α-C₃P may find use in preparing calcium phosphate mineral cements, where it may be a calcium source, where the cement may be prepared from one or more calcium sources. Generally, the substantially phase pure α-C₃P will be milled into a particulate composition for use in preparing the cement. The particle sizes in the particulate composition may range from less than 1.0 to 180 μm, usually less than 1.0 to 30 μm. Although dependent on the type of milling employed, milling times may range from 0.1 to 80 hr, usually 0.5 to 4 hr. Any convenient means of milling may be employed, including ball milling, jet milling, SWECO® milling, attritor milling, hammer milling, planetary ball milling, and the like.

The characteristics of the α-C₃P composition which is used as a calcium source can affect the functional characteristics of the cement in which it is included. For example, the mean particle size of the particles in, as well as the surface area and the particle size distribution of, a milled α-C₃P composition used in a calcium phosphate mineral cement can influence the setting time of the cement and the compressive strength of the calcium phosphate mineral produced from the cement. Other factors which may influence the character of the calcium phosphate cement include the purity of the α-C₃P composition.

Figure 3A:
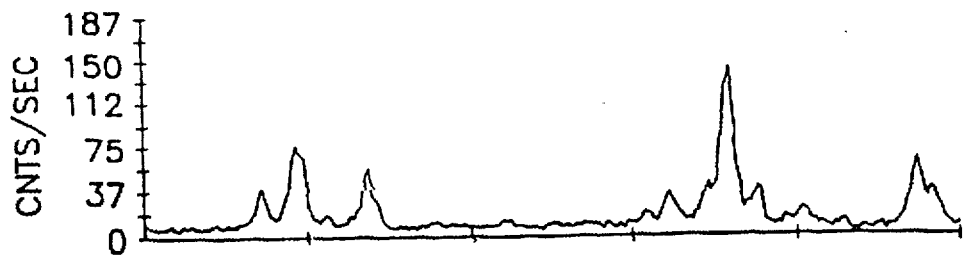
FIGS. 3a–3d provide X-ray diffraction patterns for jet milled, wet ball milled, SWECO® milled and attritor milled preparations of $\alpha$-$C_3P$, respectively.
Figure 3B:
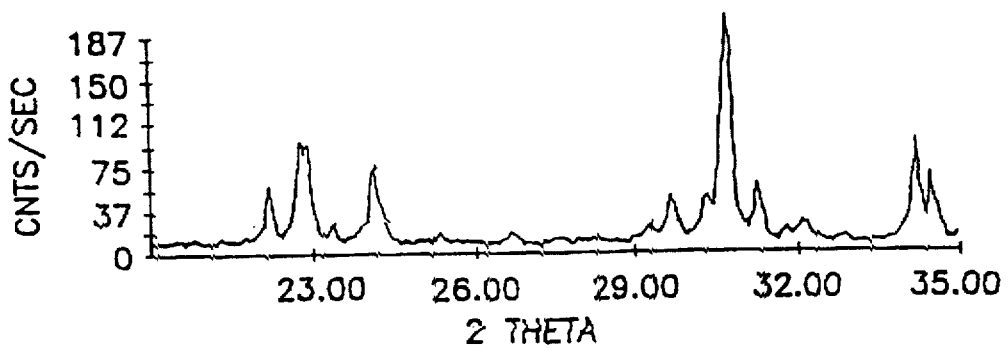
Figure 3C:
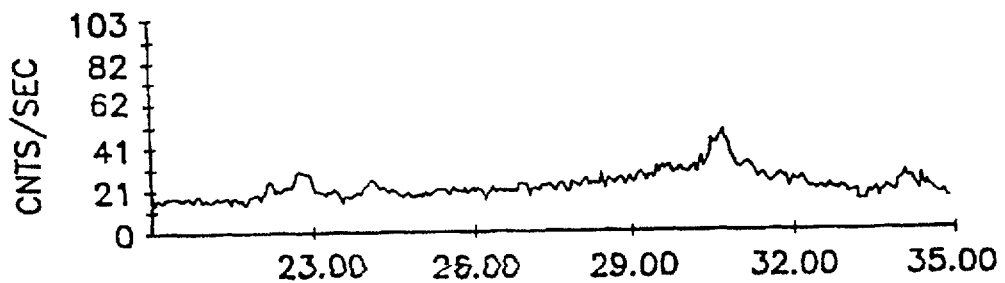
Figure 3D:
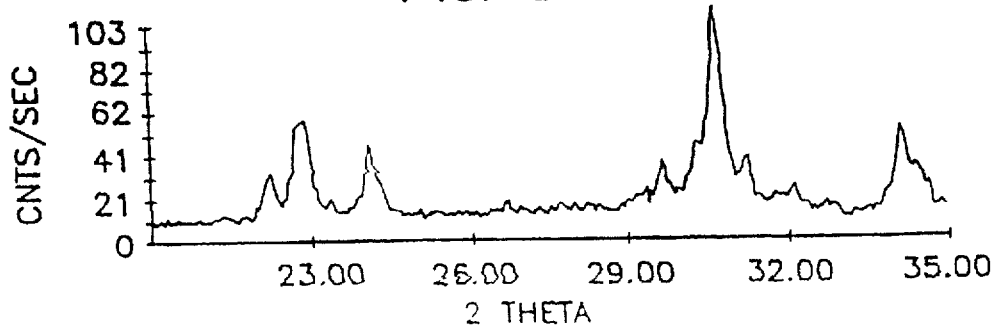
Figure 4B:
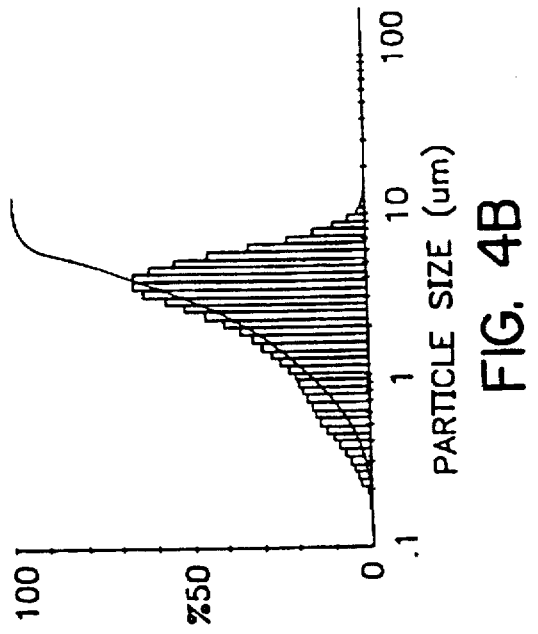
FIGS. 4a–4d provide particle size distribution curves for attritor, wet ball milled, SWECO® and jet milled preparations of $\alpha$-$C_3P$, respectively.
Figure 4D:
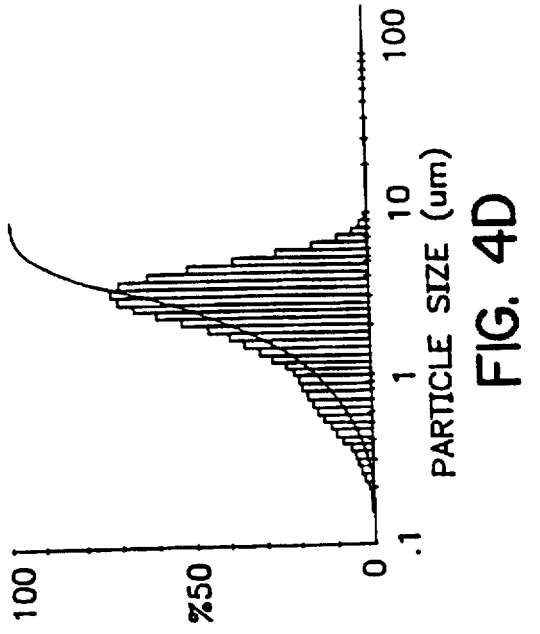
Figure 4A:
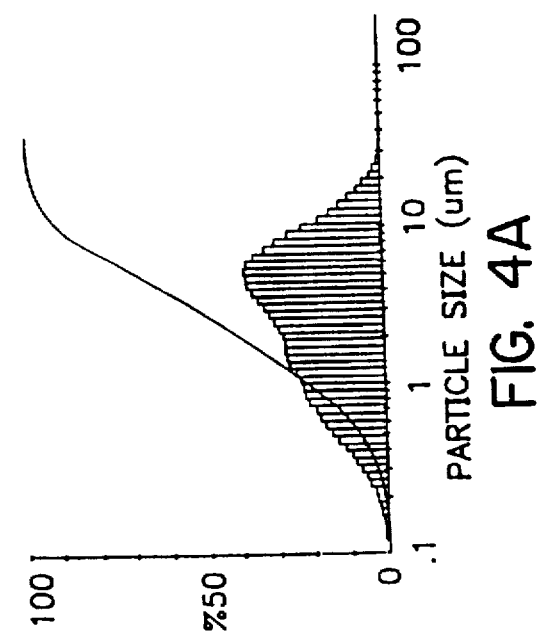

Of particular interest are α-C₃P compositions which are sufficiently reactive for use in the preparation of cements which are intended to set in situ, i.e. reactive α-C₃P compositions. Such reactive α-C₃P compositions will: (a) comprise particles having a mean diameter ranging from 3 to 5 μm, usually being about 4 μm; (b) have a surface area ranging between about 2.5 and 3.5 m²/gm, usually being about 3 m²/gm; and (c) have a particle size distribution ranging from less than 1 to 30 μm. Of particular interest is a particle size distribution which is substantially the same as the particle size distribution shown in FIG. 4a. As is known to those skilled in the art and as is used in this application, "substantially the same as" means that the actual particle size curve may differ from that shown in FIG. 4a by as much as 10% and still be considered the same as the curve shown in FIG. 4a. As seen in FIG. 4a, the particle size distribution may be graphically represented, where the number of particles is given as a function of size, as a curve having a broad peak and a leading shoulder, where the leading shoulder is displaced from the broad peak by between 2 and 4 μm, usually by about 3 μm, with the broad peak occurring at between 4 and 6 μm, more usually at about 5 μm. The reactive α-C₃P composition will also preferably have an X-ray diffraction pattern which is the same as that shown in FIG. 3d, where the term "same" as used here is understood to mean a diffraction pattern which can vary from that shown in FIG. 3d by as much as 10%, including an X-ray diffraction pattern which corresponds exactly to that shown in FIG. 3d.

In addition to the above characteristics, the reactive α-C₃P composition will preferably be substantially free of impurities, such as impurities derived from milling media, e.g. zinc oxide, iron oxide and the like, where substantially free of impurities means at least 90% free, usually at least 95% free, and preferably at least about 99% free of impurities. Although any convenient means of milling a substantially phase pure α-C₃P product to obtain a composition having these characteristics may be employed, one preferred method of milling is attritor milling. Attritor mills are known to those skilled in the art and are described in Richardson, Modern Ceramic Engineering (1982) and Treatise on Materials Science Technology, Volume 9 (ed. Franklin Wang) (1976). Although the milling media of the attritor mill may be any convenient material, one type of material that is particularly suited for milling the α-C₃P product is yttria stabilized zirconia because of its extreme hardness and wear resistance. When the α-C₃P is attritor milled, typical milling times will range from 10 min. to 24 hr, usually from 30 min. to 2 hr.

Although the above method for producing a reactive tricalcium phosphate composition was described in terms of using the subject phase pure α-C₃P as the tricalcium phosphate source, other forms of tricalcium phosphate may also be milled in accordance with the subject method to provide a reactive tricalcium phosphate composition. Other forms of tricalcium phosphate which are known to those skilled in the art include β-tricalcium phosphate, α'-tricalcium phosphate and the like.

The reactive C₃P composition of the subject invention, e.g. that prepared from α-C₃P, finds application in the preparation of calcium phosphate cements, such as those described in European Patent No. 0416761, EP-A- 0 347, 028 and WO 92/02453, the disclosures of which are herein incorporated by reference. Calcium phosphate minerals can be produced by mixing a phosphoric acid source substantially free of unbound water, a calcium source, and a lubricant to produce a physiologically acceptable, kneadable product which is capable of setting into a solid mass. Where apatitic products are desired, the preferred calcium to phosphate ratio is between about 1.0 and about 2.0, and preferably about 1.67. Optionally, crystalline nuclei, particularly hydroxyapatite or calcium phosphate crystals, may also be included in the mixture. When used in the preparation of calcium phosphate mineral cements, the subject reactive α-C₃P preparations may be combined with at least one additional calcium source, including β-C₃P, tetracalcium phosphate (C₄P), calcium carbonate (CaCO₃), or calcium hydroxide (Ca(OH)₂). The reactive α-C₃P compositions may also find use in the preparation of calcium phosphate mineral cements where the calcium source has at least partially reacted with the acidic phosphate source. Such cements are described in co-pending U.S. application Ser. Nos. 08/096,161, filed Jul. 22, 1993 and 08/294,325 filed Aug. 23, 1994, U.S. Pat. No. 5,496,399, the disclosures of which are hereby incorporated by reference.

In preparing calcium phosphate cements where the subject reactive α-C₃P composition is employed in the calcium phosphate cement, the calcium source will preferably be in the form of a mixture comprised of at least 20 percent of reactive α-C₃P composition, usually at least 50 percent of reactive α-C₃P composition, and more usually at least 70 percent of reactive α-C₃P composition, where the remaining percentage of calcium source includes β-C₃P, TCP, CaCO₃ or Ca(OH)₂. Where calcium hydroxide is used as an additional source of calcium, it is typically present in the mixture from about 0.1 to about 10 weight percent, preferably 1 to 2 weight percent, of the dry ingredients of the mixture. Particularly where a dahllite product is preferred, CaCO₃ may be used as an additional source of calcium and will preferably be present in the mixture at from about 2 to about 40 weight percent, or as necessary to provide a final product having from about 3 to about 8 weight percent carbonate. When calcium carbonate is used as an additional source of calcium or carbonate, the reaction will result in a relatively lower temperature rise as compared to neutralizing agents such as calcium hydroxide and calcium oxide; however, there is substantial evolution of gas which must be released during mixing. Depending on the nature of the acid source, the calcium source will usually be provided from about 1 to about 95 weight percent, and preferably from about 40 to about 90 weight percent of the dry ingredients of the reaction mixture, or as required to provide the proper calcium to phosphate molar ratio for the desired product.

The phosphoric acid source for the reactions may be any partially neutralized phosphoric acid, particularly up to and including complete neutralization of the first two protons, as in calcium phosphate dibasic, and more particularly the first proton, as in monocalcium phosphate monohydrate (MCPM). Alternatively or additionally, it can consist of orthophosphoric acid, preferably in a crystalline form, that is substantially free of combined water. The acid source will generally be about 1.0 to about 40 weight percent of the dry ingredients of the mixture.

Suitable lubricants or liquid ingredients may include any lubricant selected from a group of physiologically compatible liquids including, but not limited to, water or purified forms thereof, aqueous alkanols, e.g. glycerol, where the alkanol is present in minor amounts, preferably less than about 20 volume percent, pH buffered or non-buffered solutions, solutions described in U.S. Pat. No. 5,336,264, the disclosure of which is herein incorporated by reference, and the like.

The dry ingredients may be prepared prior to combination with the liquid ingredients as a mixture and subsequently mixed with the liquid ingredients until a substantially uniform dispersal of ingredients is obtained. As the various components are added, mixing will be used to combine the ingredients and can be used to regulate the extent of reaction between the components of the cement. Any or all of the ingredients may be added prior to the initiation of mixing or prior to the completion of mechanical mixing. Methods of mixing can include ball milling, Brabender mixing, rolling between one or more rollers and a flexible container, or the like. Preferably, mixing will be thorough and will occur for a relatively short time or until a uniform dispersal of ingredients is obtained. Where gases are evolved, mixing will allow the release of large pockets of gas.

After mixing, the mixture is allowed to anneal while remaining quiescent, followed by an extended period of time during which the mixture hardens. During hardening, an essentially complete reaction of the combined calcium and phosphoric acid sources occurs, crystal growth occurs, and the product becomes an integral mass.

Calcium phosphate cements prepared from the subject reactive α-C₃P preparations are biocompatible, having a pH in the range of about 5–8, usually in the range of about 6–7.5. The cements are prepared so that they can be administered in an environment having a temperature in the range of about 0°–45° C., and typically at about normal physiological temperature, 37° C. The calcium phosphate products have low or no toxicity when prepared in accordance with described methods, are substantially inert, have substantially no detrimental interactions with various host components, i.e. they are nonallergenic and non-immunogenic, and are readily implantable.

When used as cements or fillers, the calcium phosphate cements which are prepared with the α-C₃P compositions of the subject invention will bond to other apatites when applied to an apatitic surface, such as bone or teeth which are mainly comprised of dahllite and collagen. The applicable compositions are able to adhere and bond to surfaces that are wet or coated with saliva, blood or lymphatic fluid, will fill voids, and conform to irregular surfaces such as concavities and convexities. The compositions may be applied as a continuous mass without the formation of fragments or loose particles to a significant degree. Furthermore, compositions partially comprised of the subject products are found to be structurally compatible in providing for the structural functions of replaced bone.

The following examples are offered by way of illustration and not by way of limitation.

EXPERIMENTAL

Example 1. Synthesis of Room Temperature Stable, Phase Pure $\alpha$-$C_3P$, Method 1

2 moles of $CaHPO_4$ and 1 mole of $CaCO_3$ were added to 272 ml of water to produce a slurry with a calcium to phosphate ratio of 1.5:1. The resultant slurry was poured into a filter press and the solids were separated from the liquid at a pressure of 10 psi. The resulting filter cake was then heated in a furnace to about 1400° C. for four hours.

To quench the heated filter cake, the cake was removed from the furnace and placed in a large pan where it was carefully crushed with a large pestle to form smaller pieces. When exposed to ambient room temperature conditions, the temperature of these pieces dropped 700° C. over a period of about 30 s, and then continued to drop to room temperature. XRD analysis of the cooled pieces revealed that the pieces were composed of substantially phase pure $\alpha$-$C_3P$. See FIG. 1.

Figure 2:
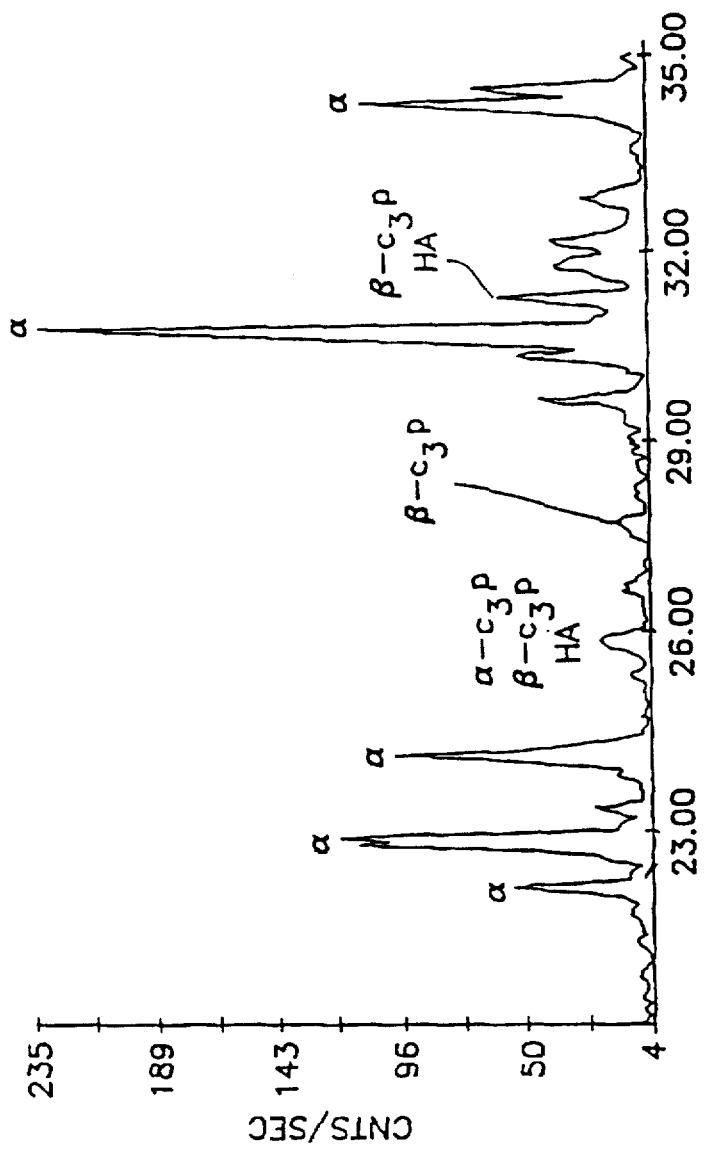
FIG. 2 is an X-ray diffraction pattern for a commercially available $\alpha$-$C_3P$ sold as Apatite Liner by Sankin Industries, Japan.

XRD patterns in this and subsequent experiments were obtained by scanning reacted calcium phosphate compositions at various reaction times. Powder x-ray diffraction measurements were performed on biomaterial samples ground with a mortar and pestle, packed in aluminum sample holders, and scanned with a Philips XRG 5000 fitted with a 42271/0 goniometer using copper $k\alpha$ radiation. Samples were scanned over a $2\theta$ range of 20° to 35° at a scan rate of 3°/minute and a step size of 0.02.

Where the rate of temperature drop was not sufficiently rapid, hydroxyapatite was identified in the resultant product, indicating that the resulting product was not phase pure. To compare the purity of the $\alpha$-$C_3P$ obtained from this method to commercially available $\alpha$-$C_3P$, XRD analysis was also made of an $\alpha$-$C_3P$ product sold by Sankin Industries, Japan (marketed as Apatite Liner). See FIG. 2. The commercially available $\alpha$-$C_3P$ was not pure $\alpha$-$C_3P$, but also comprised $\beta$-$C_3P$ and hydroxyapatite.

Example 2. Synthesis of Reactive $\alpha$-$C_3P$, Method 2

1 mole of MCPM and 2 moles of $CaCO_3$ were combined 316 ml water to obtain a slurry having a calcium to phosphate ratio of 1.5:1. The resultant slurry was poured into thin molds (shallow dishes), where the $CaCO_3$ and MCPM were allowed to react. The resultant reaction product was labeled "greenware." The greenware was heated in a furnace to 1400° C. for 4 hours. The 1400° C. greenware was then removed from the furnace and placed in a porcelain mortar, thereby quenching the greenware.

The rate of quenching of the heated greenware was important in the formation of the final product. It was found that where the temperature of the heated material was dropped by 600° C. over a period of 2 min, a room temperature stable, substantially phase pure $\alpha$-$C_3P$ product, as revealed by XRD analysis, was obtained. If the temperature was not dropped by at least 600° C. over a time of 2 min, the resultant tricalcium phosphate product would comprise $\beta$-$C_3P$ in addition to $\alpha$-$C_3P$.

Example 3. Synthesis of Reactive $\alpha$-$C_3P$, Method 3

Stoichiometric amounts of MCPM and $CaCO_3$ are combined to yield a composition having a calcium to phosphate ratio of 1.5:1. The composition is pressed into pellets. The pellets are then placed on a conveyer which passes them through a heat zone where the temperature is 1400° C. The conveyor belt is moved at a rate where the pellets remain in the heat zone for 4 hr. At the end of the heat zone, the temperature of the pellets is rapidly lowered by allowing the pellets to fall off of the conveyor into a cooled heat sink.

Example 4. Calcium Phosphate Mineral Production from Cements Comprising Reactive $\alpha$-$C_3P$ Preparations Calcium phosphate minerals were produced by stoichiometrically combining reactive $\alpha$-$C_3P$ as produced in Example 1, where the $\alpha$-$C_3P$ had been ball milled to obtain a composition with particles ranging in size from less than 1 to 100 µm, with orthophosphoric acid (oPA), calcium carbonate ($CaCO_3$) or calcium hydroxide ($Ca(OH)_2$), and an aqueous sodium phosphate solution, where the species and concentration of sodium phosphate in solution were adjusted to attain consistent rheological properties between the different formulations. Depending on the formulation, the amount of aqueous sodium phosphate combined with the dry ingredients ranged from 6 ml to 8.25 ml. Both the $CaCO_3$ and $Ca(OH)_2$ served as additional sources of calcium in the reaction. Carbonate was required for the synthesis of carbonated apatites, and further acted as a pH buffer.

Several different formulations comprising the above components were tested to determine setting times[†] and compressive strengths[††] for the various formulations. The results from these tests are provided in Table 1 below.

[†]To determine the setting times, an indentation test was employed. In the indentation test, calcium phosphate compositions were mixed and placed into a sample ring that is 32 mm Outer Diameter, 25 mm Inner Diameter, and 5 mm thickness. Using a spatula, the material was pushed into the sample rings and the top was smooth and flush with the top of the set rings. Within 2 minutes the set rings were carefully slid off the flat surface on which they were prepared and submersed in 37° C. bovine serum and placed in an incubator. Samples were cured for 10 minutes, at which time they were removed from the incubator and tested. A Gilmore needle apparatus was employed. The crosshead speed was set at 0.6 in/min., crosshead travel was set at 0.05 inches, and the electronic load limit was set at a maximum of 100 pounds. After the Gilmore needle apparatus was calibrated (prior to sample prep.), the needle was pressed into the sample 0.05 inches and the load required to push the needle this distance was measured.

[††]To determine the compressive strength for the various formulations, a test derived from the ASTM F451 Test for measuring the compressive strength of bone cement (PMMA) was employed. Calcium phosphate compositions were mixed and back filled into syringes. The material was then ejected from the syringe into compression dies which have cylindrical holes measuring 6 mm diameter and 12 mm in length (thickness). The dies were overfilled with material which was finger packed (pressurized). Excess material was wiped away, additional material was overfilled and finger packed a second time. The excess material was then spread over the die faces to yield a thin coating. The other side was also coated with a thin layer of material. The die was then placed into a small ziplock bag which was placed within a slightly larger bag and filled with 37° C. bovine serum and submersed into a water bath within an incubator held at 37° C. and 100% RH. Samples were cured 24 hours, the thin layers of material were polished off, removed from the dies and then tested on an Instron. The settings on the Instron were a crosshead speed of 0.1 in/min., with a maximum load of 400 pounds. Samples were placed on platens and crushed.

TABLE 1

| Formula | Indentation Strength (lbs) | Compression Strength (MPa) |
| --- | --- | --- |
| Mixture #1 1.919 g oPA | 15 min. −19.81 15 min. −16.00[†] | 20.73 ± 1.87 |

TABLE 1-continued

| Formula | Indentation Strength (lbs) | Compression Strength (MPa) |
|---|---|---|
| 9.110 g $C_3P$ | 30 min. −38.5 | |
| 3.190 g $CaCO_3$ | | |
| 0.783 $Ca(OH)_2$ | | |
| sufficient 0.75 m $Na_3PO_4$ to reach | | |
| a liquid to solid ratio of 0.6 | | |
| Mixture #2 | 15 min. −18.5 | 44.25 ± 2.6 |
| 1.326 g oPA | 20 min. −38.77 | |
| 10.50 g $C_3P$ | 30 min. −58.0 | |
| 2.550 g $CaCO_3$ | | |
| 0.632 g $Ca(OH)_2$ | | |
| sufficient 0.25 m $Na_2HPO_4$ to reach | | |
| a liquid to solid ratio of 0.45 | | |
| Mixture #3 | 16 min. −44.5 | 34.73 ± 2.33 |
| 0.690 g oPA | 17 min. −37 | |
| 12.01 g $C_3P$ | 18 min. −37 | |
| 1.845 g $CaCO_3$ | | |
| 0.459 g $Ca(OH)_2$ | | |
| sufficient 0.25 m $Na_2HPO_4$ to reach | | |
| a liquid to solid ratio of 0.45 | | |
| Mixture #4 | LOW | 30.44 |
| 2.989 g oPA | | |
| 9.918 g $C_3P$ | | |
| 2.400 g $CaCO_3$ | | |
| 0.589 g $Ca(OH)_2$ | | |
| sufficient 0.25 m $Na_2HPO_4$ to reach | | |
| a liquid to solid ratio of 0.52 | | |
| Mixture #5 | Not Tested | 36.04 |
| 1.450 g oPA | | |
| 11.47 g $C_3P$ | | |
| 1.666 g $CaCO_3$ | | |
| 0.411 g $Ca(OH)_2$ | | |
| sufficient 0.25 m $Na_2HPO_4$ to reach | | |
| a liquid to solid ratio of 0.45 | | |
| Mixture #6 | 15 min. −0.32 | 41.85 ± 2.51 |
| 0.760 g oPA | 20 min. 0.81 | |
| 13.16 g $C_3P$ | 30 min. 7.31 | |
| 1.276 g $CaCO_3$ | | |
| 0.215 g $Ca(OH)_2$ | | |
| sufficient 0.25 m $Na_2HPO_4$ to reach | | |
| a liquid to solid ratio of 0.45 | | |
| Mixture #7 | 15 min. −43.0 | 34.41 ± 1.96 |
| 1.11 g oPA | 20 min. −37.9 | |
| 12.30 g $C_3P$ | 30 min. −91.0 | |
| 1.276 g $CaCO_3$ | | |
| 0.314 g $Ca(OH)_2$ | | |
| sufficient 0.75 m $Na_3PO_4$ to reach | | |
| a liquid to solid ratio of 0.45 | | |

†Lower indentation strength denotes sample preparation problem.

The above results show that calcium phosphate cements which are prepared with the subject room stable, substantially phase pure α-$C_3P$ will provide a calcium phosphate mineral product with high compressive strength. However, because of the relatively long setting time of these formulations, cements comprising the ball milled α-$C_3P$ composition are not suitable for use where rapid setting of cement is required.

Example 5. Preparation of α-$C_3P$ Compositions

One large lot (about 10 Kg) of room temperature stable, substantially phase pure α-$C_3P$ prepared in accordance with the method of Example 1 was divided into four equal portions. Each portion was subjected to a different milling procedure to obtain an α-$C_3P$ composition.

The first portion was milled using an attritor mill to obtain an α-$C_3P$ composition. The attritor mill used for milling the α-$C_3P$ product comprised a large, alumina lined mill jar which contained a milling shaft with several yttria stabilized zirconia shafts projecting from it at various angles. In operating the mill, the milling shaft was turned at 350 rpm. Also included in the mill jar were thousands of 5 mm cylinders of yttria stabilized alumina. Following introduction of the α-$C_3P$ into the attritor mill, the mill was run for 60 min. Every 10 minutes, 1.5 ml anhydrous ethanol was added to the mill to aid in milling efficiency.

The second portion was milled by Fluid Energy Aljet (Pennsylvania) where the α-$C_3P$ was first introduced into the mill at a feed rate of 17 lbs/hr at 10 psig and then introduced to the mill at a rate of 5 lbs/hr at 110 psig. The second step was repeated four additional times. The third portion was milled in the presence of ethanol by Norian Corporation using a wet ball mill for 18 hr. The fourth portion was milled by Sweco (Kentucky) using a SWECO® mill for 78 hr.

The characteristics of the four different α-$C_3P$ compositions obtained using the various milling methods are provided in Table 2 below.

TABLE 2

Figure 4C:
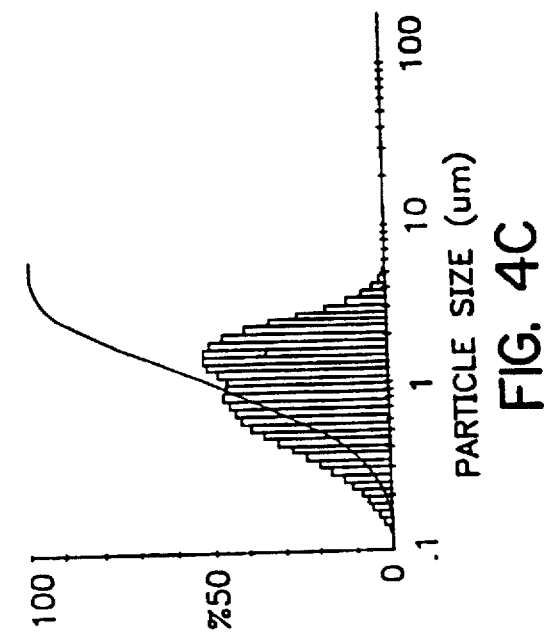

| Milling Method | Particle Size Distribution† | Mean Part. Diam. (μm) | Surface Area ($m^2$/gm)†† |
|---|---|---|---|
| Attrition | See FIG. 4a | 4.40 | 2.78 |
| Jet | See FIG. 4b | 2.84 | 1.79 |
| Wet Ball Milling | See FIG. 4c | 3.26 | 2.10 |
| SWECO* | See FIG. 4d | 1.3 | 7.88 |

†Particle size distributions of milled tricalcium phosphate samples were determined by a Malvern Mastersizer MS20 unit. Approximately 1 gram of sample was placed in a sample cup, followed by the addition of ~30 ml isopropyl alcohol to disperse the dry sample. Next, the sample cup was placed on a stir plate and an ultrasonic horn was immersed into the sample cup. This technique utilized a laser source which was directed through the slurry containing the particles to be analyzed. Prior to running a sample the device was aligned and calibrated, and a background was determined by passing isopropyl alcohol through the sample chamber. The amount of sample was determined by adding enough sample to yield an obscuration value between 0.2 and 0.3. The sample was run and the results were calculated automatically. The mean diameter, and distribution, were obtained.

††The surface area measurements were performed on milled tricalcium phosphate samples using a Micromeretics Gemini 2360 BET Surface Area Analyzer. Between 1 and 2 grams of sample was placed within the sample holder and an exact weight was recorded. A rubber stopper was placed on the sample holder which was placed within a degassing chamber on the machine. A needle-like gas line was carefully pushed into the sample powder which flowed nitrogen gas through the sample. This nitrogen gas flow was used as a carrier gas to drive off any absorbed gases. The sample tubes were then placed within a furnace lined degassing chamber where the temperature was set at 250° C. Samples were degassed for greater than 12 hours prior to testing. After degassing, the samples were sealed and allowed to cool. Once equilibrated to ambient conditions the samples were placed on the machine, sample identification, weight and ambient parameters were keyed in and the sample was run. In this method the sample was submersed in a liquid nitrogen bath and equilibrated to that temperature. Nitrogen gas was passed through the sample. After equilibration, the desorbed nitrogen molecules from the particle surfaces were detected as they traveled back out of the sample tube. Five sample points were taken, and from these points the specific surface area was determined.

The attritor milling resulted in an α-$C_3P$ composition which comprised the least impurities attributable to the particular milling media employed. The attritor milled α-$C_3P$ appeared white, while the ball milled α-$C_3P$ appeared gray, the jet milled α-$C_3P$ appeared light gray and the SWECO® milled α-$C_3P$ appeared brown.

The structure of the crystal lattice of the various milled α-$C_3P$ compositions was compared using XRD analysis. FIG. 1 provides the XRD pattern for sintered α-$C_3P$, revealing a sharp peak around 30.00, which is indicative of a highly ordered crystal lattice structure. The XRD patterns for the jet milled and ball milled α-$C_3P$ compositions, FIGS. 3a & 3b respectively, reveal a slightly less ordered crystal lattice structure than the sintered α-$C_3P$. The XRD pattern for the SWECO® milled α-$C_3P$ composition, FIG. 3c, reveals a highly disrupted, very small perfect crystal lattice structure. Finally, the XRD pattern for the attritor milled α-$C_3P$ composition, FIG. 3d, shows that attritor milling results in a composition with a more defective crystalline structure of smaller average crystal dimensions than ball or jet milled α-C₃P, but a more ordered crystalline structure with larger average crystal dimensions than SWECO® milled α-C₃P.

Example 6. Reactivity of the Various α-C₃P Compositions

The reactivity of each type of milled α-C₃P composition prepared in Example 4 was determined by using each type of milled α-C₃P in the following cement formulation:

0.00196Ca(H₂PO₄)₂·H₂O+0.048Ca₃(PO₄)₂+0.0185 CaCO₃

For attritor, wet ball and jet milled α-C₃P, 12.65 g α-C₃P, 1.85 g CaCO₃ and 0.493 g MCPM was combined with 7.2 g 0.075 m Na₂HPO₄. For SWECO® milled α-C₃P, the above amounts of dry ingredients were combined with 9.6 g of 0.075 m Na₂HPO₄.

The reactivity was determined by measuring the setting rate for each cement and the compressive strength of the calcium phosphate mineral from each cement. The results are provided below in Table 3.

TABLE 3

| Mill Method | Indentation (>100 lbs) | Comp. Strength (MPa) |
|---|---|---|
| Attritor | <10 minutes | 62 ± 6 |
| Jet | >16 minutes | 50 ± 13 |
| Wet Ball Mill | >16 minutes | 38 ± 7 |
| SWECO ® | ~15 minutes | 12 ± 5 |

As is apparent from the above results, the type of milling used to prepare a particular α-C₃P composition has a significant impact on the calcium phosphate mineral cements which comprise it. The rate of strength attainment was similar for the cements comprising the jet, wet ball and SWECO® milled materials. The attritor milled α-C₃P in the cement formulation passed the maximum load of 100 lbs in less than 10 minutes when submerged in serum equilibrated at 37° C. Since a setting time of 10 minutes is considered to be desirable for clinical applications, where the cement composition is intended to set in situ, cements comprising the attritor milled α-C₃P composition had the best setting characteristics of the cements studied.

Functionally, cements using SWECO® milled α-C₃P yielded a very dry paste which was not injectable and was difficult to work with. Furthermore, the compressive strength of the ultimate calcium phosphate mineral was significantly lower than the compressive strength obtained with cements prepared using the attritor milled α-C₃P.

It was concluded that attritor milling provided a suitably reactive α-C₃P composition for use in calcium phosphate cements, because it provided a cement which set in an ideal amount of time and produced a calcium phosphate mineral with high compressive strength. More specifically, the attritor milling provided a α-C₃P composition which had the requisite particle size distribution required to provide a cement with clinically appropriate setting and strength characteristics. Although the other milling methods studied did not provide an α-C₃P with the requisite particle size distribution, varying the milling parameters, e.g. milling times, may have yielded an α-C₃P composition with a particle size distribution similar to the attritor milled composition.

It is evident from the above examples and discussion that a method for preparing a room temperature stable, substantially phase pure α-C₃P product is provided. The subject α-C₃P product is suited for use in the preparation of calcium phosphate cements, where it imparts high tensile strength to the products formed from the cements. Also provided is a method for milling the subject α-C₃P product into an α-C₃P composition that is sufficiently reactive for use in the preparation of cements which are designed to set in situ.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A calcium phosphate cement formulation for use in the preparation of a calcium phosphate mineral by combining dry ingredients of said cement with a lubricant to produce a kneadable product capable of setting into said calcium phosphate mineral in less than 10 minutes, said formulation comprising as dry ingredients:

reactive tricalcium phosphate consisting of particles having a mean diameter of 3 to 5 μm and a surface area ranging from about 2.5 to 3.5 m²/gm;

at least one additional calcium source; and a partially neutralized phosphoric acid source.

2. The cement formulation according to claim 1, wherein said reactive tricalcium phosphate comprises particles of α-tricalcium phosphate.

3. The cement formulation according to claim 1, wherein said at least one additional calcium source is CaCO₃.

4. The cement formulation according to claim 1, wherein said partially neutralized phosphoric acid source is Ca(H₂PO₄)₂·H₂O.

5. A kit comprising the calcium phosphate cement formulation of claim 1 and a physiologically compatible lubricant.

6. The kit according to claim 5, wherein said physiologically compatible lubricant is an aqueous solution of Na₂HPO₄.

7. A calcium phosphate cement formulation for use in the preparation of a calcium phosphate mineral by combining dry ingredients of said cement with a lubricant to produce a kneadable product capable of setting into said calcium phosphate mineral in less than 10 minutes, said formulation comprising as dry ingredients:

reactive α-tricalcium phosphate consisting of particles having a mean diameter of 3 to 5 μm and a surface area ranging from about 2.5 to 3.5 m²/gm;

CaCo₃;

Ca(H₂PO₄)·H₂O.

8. The cement formulation according to claim 7, wherein said CaCO₃ is present in from about 2 to 40 weight % of said formulation.

9. The cement formulation according to claim 7, wherein said Ca(H₂PO₄)₂·H₂O is present in from about 1 to 40 weight % of said formulation.

10. A calcium phosphate cement formulation for use in the preparation of a calcium phosphate mineral by combining dry ingredients of said cement with a lubricant to produce a kneadable product capable of setting into said calcium phosphate mineral in less than 10 minutes, said formulation comprising as dry ingredients:

reactive α-tricalcium phosphate consisting of particles having a mean diameter of 3 to 5 μm and a surface area ranging from about 2.5 to 3.5 m²/gm;

$CaCO_3$;

$Ca(H_2PO_4) \cdot H_2O$;

wherein the molar ratio of said reactive α-tricalcium phosphate to said $CaCO_3$ to said $Ca(H_2PO_4) \cdot H_2O$ is 0.048 to 0.0185 to 0.00196.

11. A kit comprising the calcium phosphate cement formulation of claim 10 and an aqueous solution of $Na_2HPO_4$.

12. A kneadable product capable of setting into a solid mass comprising the cement formulation of claim 10 in combination with a physiologically compatible lubricant.

13. The kneadable product according to claim 12, wherein said physiologically compatible lubricant is an aqueous solution of $Na_2HPO_4$.

* * * * *